United States Patent [19]

Sam et al.

[11] 4,022,777

[45] May 10, 1977

[54] IMIDAZOQUINOXALINE FUNGICIDES

[75] Inventors: Donnie Joe Sam, Newark, Del.; Mark A. Wuonola, Cambridge, Mass.

[73] Assignee: E. I. Du Pont de Nemours and Company, Wilmington, Del.

[22] Filed: Sept. 22, 1975

[21] Appl. No.: 615,495

Related U.S. Application Data

[60] Division of Ser. No. 369,740, June 13, 1973, Pat. No. 3,919,423, which is a continuation-in-part of Ser. No. 277,604, Aug. 1, 1972, abandoned.

[52] U.S. Cl. .................. 260/250 Q; 260/250 QN; 424/250
[51] Int. Cl.² ..................................... C07D 487/04
[58] Field of Search ................. 260/250 Q, 250 QN

[56] References Cited

OTHER PUBLICATIONS

Roberts et al., "Basic Principles of Organic Chemistry," 1964, pp. 175, 533.

Katritzky et al., "Chemistry of the Heterocyclic N-Oxides," 1971, pp. 153–160.
Marvel et al., Org. Syn. Coll. II, pp. 310–312.
Elina et al., Chem. Abs. 78, 4216h (1972).
Sam et al., Chem. Abs. 80, 108578k (1974).

*Primary Examiner*—Alton D. Rollins
*Assistant Examiner*—Mark L. Berch

[57] ABSTRACT

Compounds of the formula

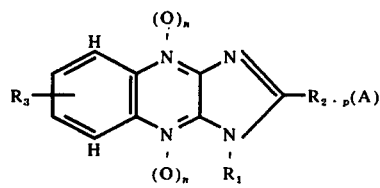

wherein $R_1$ is hydrogen, alkali metal, alkyl, substituted alkyl, alkylsulfenyl or acyl; $R_2$ is alkyl or cyclopropyl; $R_3$ is hydrogen, chlorine, bromine or fluorine; $n$ and $p$ are 0 or 1 and A is a mineral acid are useful as fungicides. A representative compound is 6-chloro-2-ethyl-1H-imidazo[4,5-b]quinoxaline.

5 Claims, No Drawings

IMIDAZOQUINOXALINE FUNGICIDES

CROSS REFERENCE TO RELATED APPLICATION

This is a division of application Ser. No. 369,740, filed June 13, 1973, now U.S. Pat. No. 3,919,423 which in turn is a continuation-in-part of our copending application Ser. No. 277,604, filed Aug. 1, 1972 now abandoned.

BACKGROUND OF THE INVENTION

This invention relates to the use of a class of imidazoquinoxalines as fungicides. Some of the compounds useful in this invention are known in the art. Schipper and Day describe imidazoquinoxalines in J. Am. Chem. Soc. 73, 5672 (1951). However, no recognition of the fungicidal activity of these compounds has been made heretofore. Fungicidal compounds having fused ring structures are known. U.S. Pat. Nos. 2,933,502; 3,541,213 and 3,657,443 teach use of benzimidazole derivatives as fungicides. U.S. Pat. No. 3,091,613 teaches the use of 6-methyl-2,3-quinoxalinedithiolcyclic-S,S-dithiocarbonate as a fungicide. These references do not suggest any fungicidal activity for the imidazoquinoxalines of this invention.

SUMMARY OF THE INVENTION

Injury due to fungi is prevented by application to the locus to be protected a fungicidally effective amount of the compounds described below. The compounds described below have systemic fungicidal activity. Thus the compounds can be applied directly to the plane parts to be protected, other parts of the plant or to the media in this the plants are growing. All such applications are included in the termi "applying to plants" as used herein. Compositions consisting essentially of these compounds are useful for controlling fungi. The fungicidal compounds are imidazoquinoxalines represented by the formula:

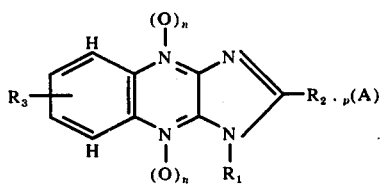

wherein
$R_1$ is hydrogen, methyl, ethyl, allyl, propargyl, chlorinated alkanesulfenyl of 1 to 2 carbon atoms and 3 to 4 chlorine atoms, methoxycarbonylmethyl, ethoxycarbonylmethyl, carboxymethyl, benzyl, 2,2,2-trichloro-1-formamidoethyl, sodium, potassium, lithium, the sodium, potassium or lithium salts of carboxymethyl or

$R_2$ is n-alkyl of 1 to 4 carbon atoms or cyclopropyl;
$R_3$ is hydrogen, bromine, chlorine or fluorine;
$R_4$ is alkyl of 1 to 9 carbon atoms; alkyl of 1 to 9 carbon atoms substituted with chlorine, bromine or methoxy; alkenyl of two to four carbon atoms; cycloalkyl of 3 to 6 carbon atoms; phenyl; phenyl substituted with bromine, chlorine, fluorine or methyl; 2-furoyl; benzyl; alkoxy of 1 to 6 carbon atoms; alkylthio of 1 to 6 carbon atoms; alkylamino of 1 to 6 carbon atoms; chlorosulfonylamino; or anilino;
$n$ is 0 or 1;
$p$ is 0 or 1;
A is $H_2SO_4$, HCl, HBr, $HNO_3$ or $H_3PO_4$ provided that
a. when $R_1$ is metal, chlorinated alkanesulfenyl or metal salt of carboxymethyl, the p is 0,
b. when $n$ is 1 and $R_3$ is hydrogen, $R_1$ is

c. when $n$ is 1 and $R_1$ is other than

$R_3$ is chlorine, bromine or fluorine
d. when $R_2$ is methyl or n-butyl and $R_3$ is hydrogen, $R_1$ is

and
e. when $R_2$ is methyl or n-butyl and $R_1$ is other than

$R_3$ is chlorine, bromine or fluorine.

Preferred for fungicidal activity are the compounds of the above formula where $R_1$ is

the compounds where $R_2$ is ethyl, the compounds where $R_3$ is chlorine and the compounds where n is 0. More preferred are the compounds where $R_1$ is

$R_2$ is ethyl, $R_3$ is chlorine, and n is 0. Within the scope of more preferred compounds, still more preferred are those compounds where $R_4$ is alkyl of 1 to 7 carbon atoms or cyclopropyl. The most preferred compounds are those where $R_2$ is ethyl, $R_3$ is chlorine and $R_1$ is cyclopropylcarbonyl, pentanoyl or hexanoyl, and $n$ is 0.

DESCRIPTION OF THE INVENTION

For the sake of clarity the nomenclature used throughout this case is based on the position numbering system for imidazoquinoxalines shown below:

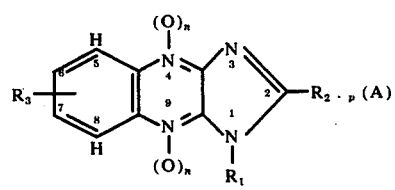

However it should be noted that the imidazole portion of the compound tautomerizes when $R_1$ is hydrogen. Although compounds will be numbered and named throughout with reference to the above formula wherein $R_3$ is a 6-substituent, both tautomers and mixtures of the tautomers are intended to be included. Similarly, products derived from the compounds where $R_1$ is H will be named with reference to the above formula, even though derivatives of either or both tautomers are intended to be included.

The compounds of this invention can be made by the processes illustrated by the following equations wherein the substituents are as previously defined.

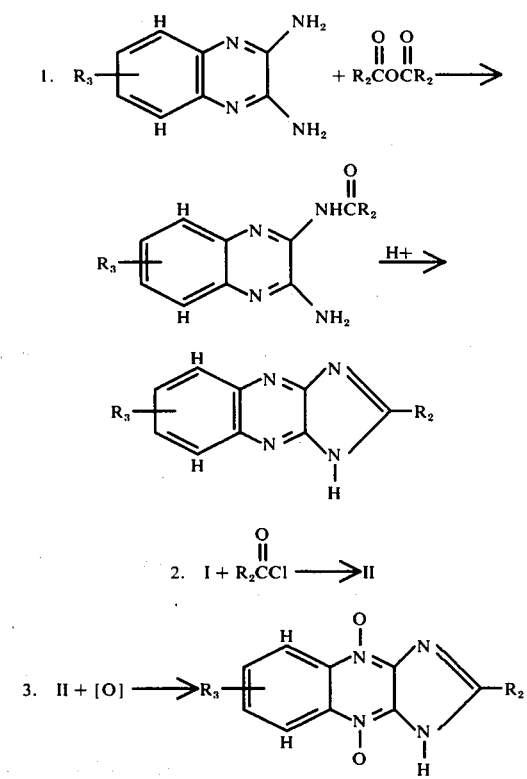

The oxidizing agent is a peracid. Suitable peracids include peracetic, performic, perbenzoic, m-chloroperbenzoic, monoperphthalic and the like.

wherein Z is the reagent(s) used to introduce the group $R_1$. Thus Z can be an acyl chloride or acid anhydride for introduction of an acyl group; an allyl, propargyl, benzyl, alkyl, or alkoxycarbonylmethyl bromide for introduction of these groups; an alkoxycarbonylmethyl bromide followed by caustic for introduction of carboxymethyl salt, followed by acidification to introduce carboxymethyl; 1,2,2,2-tetrachloro-1-formamidoethane for introduction of 2,2,2-trichloro-1-formamidoethyl; caustic for introduction of $Na^+$, $K^+$ or $Li^+$; or phenyl isocyanate, alkyl isocyanate or chlorosulfonyl isocyanate for introduction respectively of phenylcarbamoyl, alkylcarbamoyl or chlorosulfonylcarbamoyl.

The starting material for the reactions 1 and 2 shown above, a 2,3-diaminoquinoxaline, is prepared as follows:

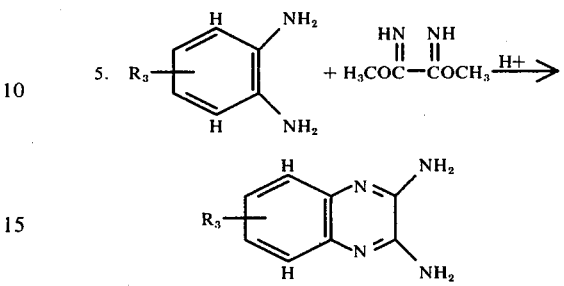

The o-phenylenediamine and substituted o-phenylenediamine reactants in the above reaction are commercially available or easily synthesized by those skilled in the art. The dimethyl oxaldiimidate reactant can be prepared by the reaction of cyanogen in an excess of methanol, preferably with a basic catalyst. Temperatures and pressures in this reaction are not critical but temperatures and pressures should be selected to handle gaseous cyanogen conveniently, as is known to those skilled in the art. Dimethyl oxaldiimidate can be isolated from the reaction mixture by distillation. The compound boils at 65° C. at 43 mm pressure. The dimethyl oxaldiimidate can also be formed and reacted with o-phenylenediamine in situ. Reaction 5 above proceeds in a methanol solvent system at room temperature. A small amount of acid is required. The preparation of 2,3-diaminoquinoxalines is also described in Hinsberg and Schwantes, Ber. 36, 4039 (1903) and Schipper and Day, J. Amer. Chem. Soc. 73, 5672 (1951).

Reaction 1 above is conveniently run at reflux in an inert solvent. Temperature is not critical and the reaction will proceed at room temperature. The second step of reaction 1 requires the presence of a small amount of acid. It is preferred to use the acid corresponding to the anhydride used in the first step. Use of a different acid can cause some substitution for $R_2$ in the product imidazoqunoxaline.

Reaction 2 proceeds in inert solvents at temperatures from room temperature to reflux. This reaction is mentioned in Schipper and Day, J. Amer. Chem. Soc. 73, 5672 (1951).

Reactions 3 and 4 also proceed in inert solvents. Temperature is not critical in these reactions. The various reagents used in reactions 3 and 4 are either commercially available or are easily synthesized by those skilled in the art.

The compounds of this invention possess outstanding fungicidal activity when employed to prevent or mitigate damage to plants by fungi. The compounds are particularly effective against powdery mildew fungi, *Erysiphaceae*. Plants are protected by preventive (before infection) and curative (after infection) treatments. Disease control is provided throughout a plant by systemic action. Isolated treatments protect across (from ventral to dorsal and dorsal to ventral) a leaf and both acropetal (upward) and basipetal (downward).

The compounds of this invention control a wide variety of powdery mildew fungus diseases of foliage, fruit and stems of growing plants without damage to the host.

The compounds of this invention provide protection from damage caused by powdery mildew fungi when applied to the proper locus by the methods described hereinafter and at a sufficient rate to exert the desired fungicidal effect. They are especially suited for the protection of living plants.

Living plants are protected from fungi by applying one or more of the compounds of this invention to the soil in which they are growing or in which they may subsequently be seeded or planted; or to plant reproductive parts prior to planting; as well as to foliage, stems and fruit of the living plant. Living plants can also be protected by dipping the root system or physically injecting the chemical or chemicals into roots or stems.

Soil applications are made from dusts, granules, pellets, slurries or solution. Rates for application of the compound of this invention to soil in which plants are or will be growing range from 1 to 100 parts per million by weight of the soil in which the roots are or will be growing.

Rates for application to seeds, tubers, bulbs or other plant reproductive parts, range from 10 to 1000 grams of active compound of this invention per 50 kilograms of planting material treated. Applications are made from dusts slurries or solutions.

Rates for application of the compounds of this invention to foliage, stems and fruit of living plants range 0.1 to b 10 kilograms of active ingredient per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries or solutions.

The compositions of the invention can contain, in addition to the active ingredient of this invention, conventional insecticides, miticides, bactericides, nematicides, fungicides, or other agricultural chemicals such as fruit set agents, fruit-thinning compounds, fertilizer ingredients and the like, so the compositions can serve useful purposes in addition to the contol of fungi. The proper choice of amounts is readily made by one skilled in the art of protecting plants from pest depredations.

The outstanding control of powdery mildew by the compounds of this invention is illustrated by a greenhouse preventive test. The compounds listed in the following table were sprayed as water suspensions on cucumber seedlings to the point of run-off. Treated seedlings were dried and inoculated with conidia of the fungus, *Erysiphe cichoracearum*. After 8 days incubation in a greenhouse, seedlings which were not treated were 85 to 100% covered with powdery mildew. Disease control readings were made by estimating the percentage of leaf surface free of disease.

| Compound | Percent Powdery Mildew Control | |
|---|---|---|
| | 16 PPM[1] | 3 PPM[1] |
| 6-chloro-2-ethyl-1H-imidazo-[4,5-b]quinoxaline | 100 | 98 |
| 6-chloro-2-ethyl-1-methyl-1H-imidazo[4,5-b]quinoxaline | 100 | 93 |
| 6-chloro-2-ethyl-1-pentanoyl-1H-imidazo[4,5-b]quinoxaline | 100 | 100 |
| 6-chloro-2-ethyl-1-hexanoyl-1H-imidazo[4,5-b]quinoxaline | 100 | 100 |
| 6-chloro-1-cyclopropylcarbonyl-2-ethyl-1H-imidazo[4,5-b]quinoxaline | 100 | 100 |
| 6-chloro-2-ethyl-1-methyoxycarbonyl-1H-imidazo[4,5-b]quinoxaline | 100 | 99 |
| 1-butylcarbamoyl-6-chloro-2-ethyl-1H-imidazo[4,5-b]quinoxaline | 100 | 97 |
| 6-chloro-2-ethyl-1-trichloromethane sulfenyl-1H-imidazo[4,5-b]quinoxaline | 100 | 92 |
| 6-chloro-2-ethyl-1H-imidazo[4,5-b]-quinoxaline hydrochloride | 100 | 89 |
| 6-chloro-2-ethyl-1H-imidazo[4,5-b]-quinoxaline sodium salt | 100 | 89 |
| 6-chloro-2-ethyl-1H-imidazo[4,5-b]-quinoxaline-4,9-dioxide | 90 | 21 |
| 1-butyryl-2-propyl-1H-imidazo-[4,5-b]quinoxaline | 100 | 96 |
| 2-ethyl-1H-imidazo[4,5-b]-quinoxaline | 85 | 41 |

[1]Concentration of active ingredient in spray suspension.

The resistance to wash-off under artificial rainfall is demonstrated by a greenhouse preventive residual test. 6-Chloro-2-ethyl-1H-imidazo( 4,5-b]qunioxaline was sprayed as a water suspension on cucumber seedlings to the point of run-off. Treated seedlings were dried overnight and then subjected to washing under simulated rainfall sprays to the extent of 1.5 cm. After the plants were dry, they were inoculated with conidia of the fungus, *Erysiphe cichoracearum*. After 8 days incubation in the greenhouse, seedlings which were not treated were 86% covered with powdery mildew. Disease control readings were made by estimating the percentage of leaf surface free of disease. Plants sprayed with 16 parts per million of the active ingredient were completely protected.

The curative activity, i.e. control of disease when treatment is applied after infection, is demonstrated by a greenhouse test with 6-chloro-2-ethyl-1H-imidazo[4,5-b]quinoxaline. Cucumber seedlings were inoculated with *E. cichoracearum* and incubated 48 hours in the greenhouse until infection was well established. Water suspensions containing 80 ppm and 16 ppm of the active ingredient were sprayed on infected plants. Disease control was 100% and 96% respectively for these two concentrations. The untreated plants had 99% of the foliage covered with powdery mildew.

The systemic activity of the compounds of this invention is demonstrated in a soil drench test on potted cucumber seedlings. Suspensions of the compounds listed below were drenched on the soil at a rate equivalent to 20 ppm of active ingredient by weight of dry soil. Care was taken to avoid contact with the foliage by any of the treatments. The seedlings were inoculated with conidia of *Erysiphe cichoracearum* and incubated in the greenhouse until untreated plants were completely covered with disease. Disease control readings were made by estimating the percentage of leaf surface free of disease.

| Compound | Percent Powdery Mildew control |
|---|---|
| 6-chloro-2-ethyl-1H-imidazo-[4,5-b]quinoxaline | 100 |
| 2-propyl-1H-imidazo[4,5-b]quinoxaline | 100 |

| Compound | Percent Powdery Mildew control |
|---|---|
| 1-methoxycarbonyl-2-methyl-1H-imidazo[4,5-b]quinoxaline | 99 |
| 2-ethyl-1H-imidazo[4,5-b]quinoxaline | 100 |
| 6-chloro-2-propyl-1H-imidazo[4,5-b]quinoxaline | 89 |
| 6-chloro-2-ethyl-1-methyl-1H-imidazo[4,5-b]quinoxaline | 100 |
| 6-chloro-2-ethyl-1-pentanoyl-1H-imidazo[4,5-b]quinoxaline | 98 |
| 6-chloro-2-ethyl-1-hexanoyl-1H-imidazo[4,5-b]quinoxaline | 92 |
| 6-chloro-1-cyclopropylcarbonyl-2-ethyl-1H-imidazo[4,5-b]quinoxaline | 100 |
| 6-chloro-2-ethyl-1-methoxycarbonyl-1H-imidazo[4,5-b]quinoxaline | 100 |
| 1-butylcarbamoyl]-6-chloro-2-ethyl-1H-imidazo[4,5-b]quinoxaline | 100 |
| 6-chloro-2-ethyl-1-trichloromethanesulfenyl-1H-imidazo[4,5-b]quinoxaline | 84 |
| 6-chloro-2-ethyl-1H-imidazo[4,5-b]quinoxaline hydrochloride | 95 |
| 6-chloro-2-ethyl-1H-imidazo[4,5-b]quinoxaline sodium salt | 96 |
| 6-chloro-2-ethyl-1H-imidazo[4,5-b]quinoxaline-4,9-dioxide | 85 |
| 1-butyryl-2-propyl-1H-imidazo[4,5-b]quinoxaline | 100 |

The systemic activity from foliage applications is demonstrated by treatments to isolated portions of cucumber seedlings which are then inoculated with E. cichoracearum. 6-Chloro-2-ethyl-1H-imidazo[4,5-b]quinoxaline was suspended at the concentration of 250 ppm in distilled water containing 250 ppm of surfactant Trem 014. Drops of this suspension were placed on young cucumber seedlings and disease control was compared with plants on which drops containing only surfactant were similarly placed. When five drops containing the compound of this invention were placed on the hypocotyl (lower stem), the entire plant was protected from powdery mildew. When a row of drops was placed only across the center of the first true leaf, the entire treated leaf, the leaf above and cotyledon below were protected from powdery mildew.

Useful formulations of the compounds of this invention can be prepared in conventional ways. They include dusts, granules, pellets, solutions, suspensions, emulsions, wettable powders, emulsifiable concentrates and the like. Many of these can be applied directly. Sprayable formulations can be extended in suitable media and used at spray volumes of from a few pints to several hundred gallons per acre. High-strength compositions are primarily used as intermediates for further information. The formulations, broadly, contain about 1 to 99% by weight of active ingredient(s) and at least one of a) about 0.1 to 20% surfactant(s) and b) about 5 to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the forumlation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd, Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

Compositions within the scope of this invention are made by well-known methods. Solutions are prepared by simply mixing the ingredients. The solubilities of the compounds of this invention are quite variable. The alkali metal salts are readily soluble in water and the 1-acyl compounds have appreciable solubility in some organic solvents. With insoluble compounds, fine grinding is of benefit. Fine solid compositions are made by blending and, usually, grinding as in a hammer or fluid energy mill. Suspensions are prepared by wet milling (see, for example, Littler, U.S. Pat. No. 3,060,084). Granules and pellets can be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8–59ff.

Formulations of this invention can also be made according to the teachings of

J. B. Buchanan, U.S. Pat. 3,576,834, H. L. Klopping, U.S. Pat. No. 3,541,213, R. R. Shaffer, U.S. Pat. No. 3,560,616, and E. Somers, "Formulation", Chapter 6 in Torgeson, "Fungicides", Vol I, Academic Press, New York, 1967.

The following Examples further illustrate the preparation of compounds of this invention. Examples 1 and 2 relate to the preparation of intermediates used to prepare the active compounds. All parts and percentages are by weight and temperatures are in degrees centigrade.

EXAMPLE 1

A solution of dimethyl oxaldiimidate (72 parts) in methanol (120 parts) was added to a slurry of o- phenylenediamine (64.8 parts) and p-toluenesulfonic acid (0.3 parts) in water (150 parts). The temperature rose to 38°. The reaction mixture was cooled and then filtered to give a tan solid. A solution of this solid in 1000 parts of hot dimethylformamide was clarified with activated charcoal, filtered, and cooled to yield 70.8 parts (74%) of pale yellow crystalline 2,3-diaminoquinoxaline, m.p. >300°.

ir (Nujol): ($\mu$) 2.89, 2.99 6.00, 7.65, 8.94, 9.12, 10.90.

EXAMPLE 2

A solution of dimethyl oxalidiimidate (48 parts) in methanol (80 parts) was added to a slurry of 4-chloro-o-phenylenediamine (56 parts) in 0.3% aqueous hydrochloric acid (60 parts). The temperature rose to 54°. The reaction mixture was cooled and filtered to give a brown solid. After washing with THF, 61.4 parts of tan solid remained (80%). Recrystallization from THF or dioxane gave light-yellow crystals of 6-chloro-2,3-diaminoquinoxaline, m.p. 300°–303°.

ir (Nujol): ($\mu$) 3.06, 3.24, 5.99, 7.30, 6.65, 8.90, 10.65, 11.58, 12.35

H nmr (DMSO-$d_6$) ($\delta$) 6.75 (br. sing., 4H, N$\underline{H}_2$); 7.28 (mult, 3H, arom.)

Using properly selected starting materials and the procedure of Examples 1 or 2 the following compounds can be prepared:

2,3-diamino-6-fluoroquinoxaline, m.p. 245°–250°
2,3-diamino-6-bromoquinoxaline, m.p. 180°–185°.

EXAMPLE 3

A solution of 20.8 parts of acetic anhydride in 100 parts of tetrahydrofuran was added to a slurry of 24.0 parts of 2,3-diaminoquinoxaline in 900 parts of tetahydrofuran. The heterogeneous reaction mixture was stirred at 25° for 20 hrs and then concentrated in vacuo to give 25 parts of 2-acetamido-3-aminoquinoxaline, mp 319° (dec.).

ir (Nujol): ($\mu$) 2.95, 6.02, 7.47, 8.36, 9.72

A solution of 19 parts of 2-acetamido-3-aminoquinoxaline in 200 parts of glacial acetic acid was heated at reflux for 30 minutes. Concentration in vacuo left a pale yellow solid. Recrystallization from ethyl acetate-methanol (2:1) gave 16.8 parts of pale yellow 2-methyl-1H-imidazo[4,5-b]quinoxaline, mp 360° (dec.). ir (Nujol): ($\mu$) 3.5–4.5 (br.), 7.47, 8.75, 8.89, 9.65, 10.75, 13.30

EXAMPLE 4

Four parts of 6-chloro-2,3-diaminoquinoxaline was combined with 3 parts of propionic anhydride n 2 parts of tetrahydrofuran. The mixture was heated for three hours during which time a thick slurry formed. The solid was collected from the hot mixture by filtration and washed twice with two parts of tetrahydrofuran. The gray solid was air-dried to give four parts of 6-chloro-2-ethyl-1H-imidazo[4,5-b]quinoxaline, m.p. 298°–300°.

EXAMPLE 5

A suspension of 5 parts of 2,3-diamino-6-chloroquinoxaline and 6 parts of butyric anhydride in 350 parts of tetrahydrofuran was heated at reflux under nitrogen for 1.5 hrs. The yellow, homogeneous reaction mixture was concentrated in vacuo to half volume, and 20 parts of butyric acid was added. After heating at reflux for 30 minutes, the solution was concentrated in vacuo to give a yellow solid. Recrystallization from THF-hexane gave 5.45 parts of nearly colorless 6-chloro-2-propyl-1H-imidazo[4,5-b]quinoxaline, m.p. 280°–282°.

ir (Nujol): ($\mu$) 3.6–4.5 l (br.), 6.66, 7.50, 8.20, 8.38, 8.53, 9.30, 10.58, 11.43, 12.10.

By the procedures of Examples 3, 4 or 5 and properly selected starting materials, the following compounds can be prepared:

|  | M.P. |
|---|---|
| 6-chloro-2-methyl-1H-imidazo[4,5-b]quinoxaline | >300° |
| 2-butyl-6-chloro-1H-imidazo[4,5-b]quinoxaline | 242–245° |
| 2-ethyl-1H-imidazo[4,5-b]quinoxaline | >300° |
| 2-propyl-1H-imidazo[4,5-b]quinoxaline | 275–277° |
| 6-chloro-2-methyl-1H-imidazo[4,5-b]quinoxaline | >300° |
| 2-butyl-6-chloro-1H-imidazo[4,5-b]quinoxaline | 242–245° |
| 6-bromo-2-ethyl-1H-imidazo[4,5-b]quinoxaline | 290–293° |
| 6-fluoro-2-ethyl-1H-imidazo[4,5-b]quinoxaline | >300° |

By substitution of the appropriate acid chloride for the anhydride used to prepare the preceding compounds, the following compound can be made:
6-chloro-2-cyclopropyl-1H-imidazo[4,5-b]quinoxaline, m.p. 291–293°

EXAMPLE 6

One part of 6-chloro-2-ethyl-1H-imidazo[4,5-b]quinoxaline was combined with 2 parts of 40% peracetic acid in 20 parts of glacial acetic acid. The mixture was heated for 1 hour at 100°. The solution was poured into 80 parts of ice water to give a bright yellow solid. One part of the desired product, 6-chloro-2-ethyl-1H-imidazo[4,5-b]quinoxaline-4,9-dioxide, m.p. 235°–238°, was recovered by filtration.

EXAMPLE 7

Five parts of 6-chloro-2-ethyl-1H-imidazo[4,5-b]quinoxaline was suspended in 30 parts of tetrahydrofuran and 1 part 55% sodium hydride in mineral oil was added portionwise to give a solution. The solvent was removed under reduced pressure to give 6 parts of 6-chloro-2-ethyl-1H-imidazo[4,5-b]quinoxaline, sodium salt, m.p. >300°.

By substitution of potassium hydride and lithium hydride for sodium hydride in the above example, the following compounds can be prepared:
6-chloro-2-ethyl-1H-imidazo[4,5-b]quinoxaline, potassium salt  6-chloro-2-ethyl-1H-imidazo[4,5-b]quinoxaline, lithium salt

EXAMPLE 8

Two parts of 6-chloro-2-ethyl-1H-imidazo[4,5-b]quinoxaline was suspended in 40 parts of methanol. One part of concentrated HCl was added to give a solution. A solid formed at once and the slurry was cooled and filtered to give 2 parts of 6-chloro-2-ethyl-1H-imidazo[4,5-b]quinoxaline hydrochloride, m.p. 280°–282°.

By substitution of sulfuric acid, hydrobormic acid, nitric acid, and phosphoric acid solutions for the hydrochloric acid of Example 8, the following salts can be made:
6-chloro-2 -ethyl-1H-imidazo[4,5-b]quinoxline dihydrosulfate, m.p. 171–176°
6-chloro-2-ethyl-1H-imidazo[4,5-b]quinoxaline hydrobromide
6-chloro-2-ethyl-1H-imidazo[4,5-b]quinoxaline hydronitrate 6-chloro-2-ethyl-1H-imidazo[4,5-b]quinoxaline trihydrophosphate

EXAMPLE 9

A mixture of 100 parts of 6-chloro-2-ethyl-1H-imidazo[4,5-b]quinoxaline, 70 parts of anhydrous potassium carbonate, 75 parts of ethyl bromoacetate, and 600 parts of anhydrous dimethylformamide was heated at 100° for 2.5 hours. The mixture was filtered and the crude product was precipitated from the filtrate by addition of 1200 parts of water, collected by filtration, washed with water, ethanol, and ether, and airdried. Recrystallization from 95% ethanol afforded 63 parts of 6-chloro-2-ethyl-1-ethoxycarbonylmethyl-1H-imidazo[4,5-b]quinoxaline, m.p. 174°–175°.

Substitution of methyl bromoacetate for ethyl bromoacetate in Example 9 provides the product: 6-chloro-2-ethyl-1-methyoxycarbonylmethyl-1H-imidazo[4,5-b]quinoxaline.

EXAMPLE 10

A solution of 30 parts of 6-chloro-2-ethyl-1-ethoxycarbonylmethyl-1H-imidazo [4,5-b]quinoxaline and 6 parts of potassium hydroxide in 500 parts of 95% ethanol was heated at reflux for 4 hours. As the saponification progressed, the potassium salt precipitated from the solution. The mixture was cooled and filtered. The product was washed with 95% ethanol, ether, and airdried to yield 26 parts of 1-carboxymethyl-6-chloro-2-ethyl-1H-imidazo [4,5-b]quinoxaline, potassium salt, m.p 259°–269°.

Substitutions of sodium hydroxide and of lithium hydroxide for potassium hydroxide in the above example afford respectively:

1-carboxymethyl-6-chloro-2-ethyl-1H-imidazo[4,5-b]quinoxaline, sodium salt
1-carboxymethyl-6chloro-2-ethyl-1H-imidazo[4,5-b]quinoxaline, lithium salt.

Acidification of any of these three salts provides 1-carboxymethyl-6-chloro-2-ethyl-1H-imidazo[4,5-b]quinoxaline.

EXAMPLE 11

To 240 ml of dry dimethylformamide warmed to 50° with added 3.5 parts of 6-chloro-2-ethyl-1H-imidazo[4,5-b and 1.75 parts of triethylamine. The resulting solution was added, with stirring, to a 500 ml round-bottomed flask containing 3.3 parts of 1-formamido-1,2,2,2-tetrachloroethane and 45 parts of dry dimethylformamide at room temperature. After standing for 75 minutes, the clear solution was poured onto a mixture of 1500 parts of ice and water. The resulting solids were collected, washed with water and dried to give 4.6 parts of 6-chloro-2-ethyl-1-(1-formamido-2,2,2-trichlorethyl)-1H-imidazo[4,5-imidazo[4,5-b]quinoxaline, decomposing at 109°.

EXAMPLE 12

A mixture of 75 parts of 6-chloro-2-ethyl-1H-imidazo[4,5-b]quinoxaline, 85 parts of thallous ethoxide, and 600 parts of 2:1 anhydrous dimethylformamide-tetrahydrofuran was stirred at room temperature for 1 hour. Allyl bromide (50 parts) was added in one portion, and the mixture was stirred for an additional hour, followed by heating for 30 minutes on a steam bath. The mixture was filtered, and the filtrate was diluted with 2000 parts of water. The filtrate was extracted with three 500-part portions of chloroform, and the combined extracts dried (potassium carbonate) and evaporated in vacuo. The residue was dissolved in 500 parts of benzene and decolorized (silica gel). The benzene was removed in vacuo and the crude product recrystallized from 95:5 ether-ethanol to yield 24 parts of 1-allyl-6-chloro-2-ethyl-1H-imidazo[4,5-b]quinoxaline, m.p. 117°–121°.

By substitution of the appropriate bromides for the allyl bromide in Example 12, the following compounds can be made:
  6-chloro-2-ethyl-1-propargyl-1H-imidazo[4,5-b]quinoxaline, m.p. 131°–145°
  1-benzyl-6-chloro-2-ethyl-1H-imidazo[4,5-b]quinoxaline.

By substitution of sodium hydride for thallous ethoxide, tetrahydrofuran for dimethylformamide-tetrahydrofuran, and dimethyl sulfate or diethyl sulfate for the allyl bromide in Example 12, the following compounds can be made:
  6-chloro-2-ethyl-1-methyl-1H-imidazo[4,5-b]quinoxaline, m.p. 192°–194°
  6-chloro-1,2-diethyl-1H-imidazo[4,5-b]quinoxaline, m.p. 144°–146°

By treatment of an ether solution of the appropriate imidazoquinoxaline with ethereal HCl the following compounds can be made:
  1-allyl-6-chloro-2-ethyl-1H-imidazo[4,5-b]quinoxaline hydrochloride, m.p. 165°–170
  1-benzyl-6-chloro-2-ethyl-1H-imidazo[4,5-b]quinoxaline hydrochloride, m.p. 193–197°
  6-chloro-2-ethyl-1-propargyl-1H-imidazo[4,5-b]quinoxaline hydrochloride, m.p. 148–150°

EXAMPLE 13

Three parts of 6-chloro-2-ethyl-1H-imidazo[4,5-b]quinoxaline was combined with 1.7 parts of hexanoyl chloride in 15 parts of tetrahydrofuran. One and one-half parts of triethylamine was added dropwise at 30° over a one-hour period. The thick reaction mixture was poured into 20 parts of water and 4 parts of 6-chloro-2-ethyl-1-hexanoyl-1H-imidazo[4,5-b]quinoxaline, m.p. 131–132°, was collected.

Through use of the general method of Example 13 and the appropriate imidazoquinoxalines and acid chlorides, the following compounds can be made:
  1-acetyl-6-chloro-2-ethyl-1H-imidazo[4,5-b]quinoxaline, m.p. 136–138°
  6-chloro-2-ethyl-1-propionyl-1H-imidazo[4,5-b]quinoxaline, m.p. 111–113°
  1-butyryl-6-chloro-2-ethyl-1H-imidazo[4,5-b]quinoxaline, m.p. 88–90°
  6-chloro-2-ethyl-1-pentanoyl-1H-imidazo[4,5-b]quinoxaline, m.p. 116°–118°
  6-chloro-2-ethyl-1-(2-methylbutanoyl)-1H-imidazo[4,5-b]quinoxaline, m.p. 63–65°
  6-chloro-2-ethyl-1-heptanoyl-1H-imidazo[4,5b-]quinoxaline, m.p. 104–107°
  6-chloro-2-ethyl-1-octanoyl-1H-imidazo[4,5-b]quinoxaline, m.p. 84°–86°
  6-chloro-2-ethyl-1-nonanoyl-1H-imidazo[4,5-b]quinoxaline, m.p. 62–64°
  6-chloro-1-decanoyl-2-ethyl-1H-imidazo[4,5-b]quinoxaline
  6-chloro-1-chloroacetyl-2-ethyl-1H-imidazo[4,5-b]quinoxaline, m.p. 138–140°
  6-chloro-1-(β-chloropropionyl)2-ethyl-1H-imidazo[4,5-b]quinoxaline, m.p. 61–63°

6-chloro-1-(γ-chlorobutyryl)-2-ethyl-1H-imidazo[4,5-b]quinoxaline, m.p. 106–108°
1-(β-bromopropionyl)-6-chloro-2-ethyl-1H-imidazo[4,5-b]quinoxaline, m.p. 183–186°
6-chloro-2-ethyl-1-methoxyacetyl-1H-imidazo[4,5-b]quinoxaline, m.p. 135–138°.
1-acryloyl-6-chloro-2-ethyl-1H-imidazo[4,5-b]quinoxaline, m.p. 125–127°
1-(3-butenoyl)-6-chloro-2-ethyl-1H-imidazo[4,5-b]quinoxaline, m.p. 190°, dec.
6-chloro-2-ethyl-1-(3-methyl-2-butenoyl)-1H-imidazo[4,5-b]quinoxaline
6-chloro-1-cyclopropylcarbonyl-2-ethyl-1H-imidazo[4,5-b]quinoxaline, m.p. 170–172°
6-chloro-1-cyclohexylcarbonyl-2-ethyl-1H-imidazo[4,5-b]quinoxaline
1-benzoyl-6-chloro-2-ethyl-1H-imidazo[4,5-b]quinoxaline
6-chloro-1-(2-chlorobenzoyl)-2-ethyl-1H-imidazo[4,5-b]quinoxaline
6-chloro-1-(2-bromobenzoyl)-2-ethyl-1H-imidazo[4,5-b]quinoxaline
6-chloro-2-ethyl-1-(2-fluorobenzoyl)-1H-imidazo[4,5-b]quinoxaline, m.p. 130–132°
6-chloro-2-ethyl-1-(p-toluoyl)-1H-imidazo[4,5-b]quinoxaline
6-chloro-2-ethyl-1-(2-furoyl)-1H-imidazo[4,5-b]quinoxaline m.p. 105–108°
6-chloro-2-ethyl-1-phenylacetyl-1H-imidazo[4,5-b]quinoxaline, m.p. 122°–126°
2-ethyl-6-fluoro-1-hexanoyl-1H-imidazo[4,5-b]quinoxaline, m.p. 110–111°
6-bromo-2-ethyl-1-hexanoyl-1H-imidazo[4,5-b]quinoxaline, m.p. 132–135°
1-acetyl-2-ethyl-1H-imidazo[4,5-b]quinoxaline-4,9-dioxide
1-acetyl-2-ethyl-1H-imidazo[4,5-b]quinoxaline, m.p. 132–134°
1-butyryl-2-ethyl-1H-imidazo[4,5-b]quinoxaline, m.p. 95–97°
1-acetyl-6-chloro-2-cyclopropyl-1H-imidazo[4,5-b]quinoxaline, m.p. 163–165°
1-acetyl-2-propyl-1H-imidazo[4,5-b]quinoxaline, m.p. 111–112.5°
6-chloro-2-ethyl-1-hexanoyl-1H-imidazo[4,5-b]quinoxaline-4,9-dioxide
1-acetyl-6-chloro-2-cyclopropyl-1H-imidazo[4,5-b]quinoxaline, m.p. 163–165°
1-acetyl-2-butyl-1H-imidazo[4,5-b]quinoxaline

EXAMPLE 14

To a suspension of 50 parts of 6-chloro-2-ethyl-1H-imidazo[4,5-b]quinoxaline in 2600 parts of tetrahydrofuran was added 106 parts of butyl isocyanate and 3 parts of triethylamine. The reaction mixture was boiled under reflux for 8 hours to produce a clear, yellow solution, and the solvent then removed in vacuo. The residue was dissolved in 750 parts of chloroform, decolorized (activated charcoal), concentrated in vacuo to a solid, and the solid recrystallized from chloroform-hexane to provide 5.7 g. of 1-butylcarbamoyl-6-chloro-2-ethyl-1H-imidazo[4,5-b]quinoxaline as a colorless solid, m.p. 116–118°.

Through use of the general method of Example 14 and the appropriate imidazoquinoxalines and isocyanates, the following compounds can be made:
6-chloro-2-ethyl-1-methylcarbamoyl-1H-imidazo[4,5-b]quinoxaline, m.p. 303–305°
2-methyl-1-methylcarbamoyl-1H-imidazo[4,5-b]quinoxaline, m.p. >300°
6-chloro-2-ethyl-1-hexylcarbamoyl-1H-imidazo[4,5-b]quinoxaline 6-chloro-1-chlorosulfonylcarbamoyl-2-ethyl-1H-imidazo[4,5-b]quinoxaline, m.p. 225–229°
6-chloro-2-ethyl-1-phenylcarbamoyl-1H-imidazo[4,5-b]quinoxaline, m.p. 304–306°
1-methylcarbamoyl-2-propyl-1H-imidazo[4,5-b]quinoxaline, m.p. 131–133°
1-butylcarbamoyl-2-propyl-1H-imidazo[4,5-b]quinoxaline, m.p. 103–105°
6-chloro-2-cyclopropyl-1-isopropylcarbamoyl-1H-imidazo[4,5-b]-quinoxaline, m.p. 146–148°

EXAMPLE 15

A solution of 6 parts of methyl chloroformate in 50 parts of tetrahydrofuran was added over 30 minutes to a suspension of 4 parts of 2-methyl-1H-imidazo[4,5-b]quinoxaline in 200 parts of tetrahydrofuran and 6 parts of pyridine. The heterogenous reaction mixture was stirred at 25° for 17 hours. Concentration in vacuo, addition of 200 parts of $CH_2Cl_2$, washing with 500 parts of 5% HCl, drying over sodium sulfate, and concentrating in vacuo left a pale yellow solid. Recrystallization from chloroform-hexane gave almost colorless 1-methoxycarbonyl-2-methyl-1H-imidazo[4,5-b]quinoxaline, m.p. 184° (dec.).

ir (Nujol): (μ) 5.67, 6.45, 7.45, 7.55, 7.79, 8.29, 9.19, 10.65

H nmr ($CDCl_3$): (δ) 3.02 (3H, sing., $CH_3$); 4.20 (3H, sing., $CH_3$); 7.67–8.33 (4H, mult., arom.)

Through use of the general method of Example 15 and the appropriate imidazoquinoxalines and chloroformates, the following compounds can be made:
6-chloro-2-ethyl-1-methoxycarbonyl-1H-imidazo[4,5-b]quinoxaline, m.p. 175–177°
1-butoxycarbonyl-6-chloro-2-ethyl-1H-imidazo[4,5-b]quinoxaline, m.p. 136–139°
6-chloro-2-ethyl-1-hexoxycarbonyl-1H-imidazo[4,5-b]quinoxaline
1-butoxycarbonyl-2-propyl-1H-imidazo[4,5-b]quinoxaline, m.p. 101–103°
1-methoxycarbonyl-2-propyl-1H-imidazo[4,5-b]quinoxaline, m.p. 132–134°.
6-chloro-2-ethyl-1-methylthiolcarbonyl-1H-imidazo[4,5-b]quinoxaline, m.p. 146–150°
6-chloro-2-ethyl-1-hexylthiolcarbonyl-1H-imidazo[4,5-b]quinoxaline

EXAMPLE 16

Two parts of 6-chloro-2-ethyl-1H-imidazo[4,5-b]quinoxaline was combined with two parts of perchloromethyl mercaptan in 60 parts of tetrahydrofuran. One part of triethylamine was added slowly dropwise at 30° over a 1-hour period. The mixture was poured into water and crude product was collected. The material was recrystallized from a chloroform:hexane mixture to give 1 part of 6-chloro-2-ethyl-1-trichloromethanesulfenyl-1H-imidazo[4,5-b]quinoxaline, m.p. 250° (dec.).

By substitution of 1,1,2,2-tetrachloroethanesulfenyl chloride for the trichloromethanesulfenyl chloride in Example 16, the following compound can be made:
6-chloro-2-ethyl-1-(1,1,2,2-tetrachloroethanesulfenyl)-1H-imidazo[4,5-b]quinoxaline.

The compounds useful in this invention can be formulated in a conventional manner as illustrated in the following examples.

EXAMPLE 17

| Wettable Powder | Percent |
| --- | --- |
| 6-chloro-1-cyclopropylcarbonyl-2-ethyl-1H-imidazo[4,5-b]quinoxaline | 25 |
| dioctyl sodium sulfosuccinate | 1.5 |
| sodium ligninsulfonate | 3 |
| low-viscosity methyl cellulose | 1.5 |
| attapulgite | 69 |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 18

| Wettable Powder | Percent |
| --- | --- |
| 6-chloro-2-ethyl-1-hexanoyl-1H-imidazo[4,5-b]quinoxaline | 50 |
| sodium alkylnaphthalenesulfonate | 5 |
| partially desulfonated sodium lignin sulfonate | 8 |
| charcoal | 4 |
| kaolinite | 33 |

The ingredients are blended, passed through a hammer mill and then an air mill to produce particles under 5 microns in average size. After reblending and sifting, the product is packaged.

EXAMPLE 19

| Aqueous Suspension | Percent |
| --- | --- |
| 6-chloro-2-ethyl-1-pentanoyl-1H-imidazo[4,5-b]-quinoxaline | 25 |
| hydrated attapulgite | 3 |
| crude calcium ligninsulfonate | 10 |
| sodium dihydrogen phosphate | 0.5 |
| water | 61.5 |

The ingredients are ground together in a ball or roller mill until the solid particles have been reduced to diameters under 10 microns.

We claim:

1. A compound of the formula

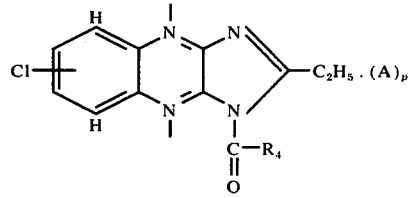

wherein
$R_4$ is alkyl of 1 to 9 carbon atoms; alkyl of 1 to 9 carbon atoms substituted with 1 chlorine or bromine atom or 1 methoxy group; alkenyl of two to four carbon atoms; cycloalkyl of 3 to 6 carbon atoms; phenyl; phenyl substituted with 1 bromine, chlorine, or fluorine atom or 1 methyl group; 2-furoyl; benzyl; alkoxy of 1 to 6 carbon atoms; alkylthio of 1 to 6 carbon atoms; alkylamino of 1 to 6 carbon atoms; chlorosulfonylamino; or anilino;
$p$ is 0 or 1;
A is $H_2SO_4$, HCl, HBr, $HNO_3$ or $H_3PO_4$.

2. A compound of the formula

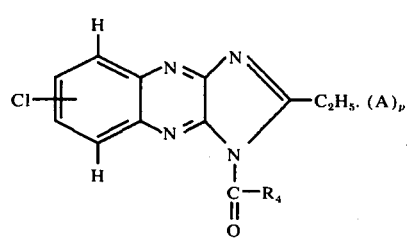

wherein $R_4$ is alkyl of 1 to 7 carbons or cyclopropyl;
A is $H_2SO_4$, HCl, HBr, $HNO_3$, or $H_3PO_4$; and
$p$ is 0 or 1.

3. The compound of claim 2 wherein $R_4$ is cyclopropyl.

4. The compound of claim 2 wherein $R_4$ is alkyl of 4 carbon atoms.

5. The compound of claim 2 wherein Rhd 4 is alkyl of 5 carbon atoms.

* * * * *